United States Patent
Ross

(10) Patent No.: US 11,583,333 B2
(45) Date of Patent: Feb. 21, 2023

(54) MAPPING VESSELS FOR RESECTING BODY TISSUE

(71) Applicant: Covidien LP, Mansfield, MA (US)

(72) Inventor: Anthony B. Ross, Boulder, CO (US)

(73) Assignee: COVIDIEN LP, Mansfield, MA (US)

(*) Notice: Subject to any disclaimer, the term of this patent is extended or adjusted under 35 U.S.C. 154(b) by 270 days.

(21) Appl. No.: 16/872,552

(22) Filed: May 12, 2020

(65) Prior Publication Data

US 2020/0268438 A1 Aug. 27, 2020

Related U.S. Application Data

(62) Division of application No. 14/923,629, filed on Oct. 27, 2015, now Pat. No. 10,653,476.
(Continued)

(51) Int. Cl.
*A61B 17/00* (2006.01)
*A61B 18/14* (2006.01)
(Continued)

(52) U.S. Cl.
CPC ...... *A61B 18/1445* (2013.01); *A61B 17/3209* (2013.01); *A61B 90/39* (2016.02);
(Continued)

(58) Field of Classification Search
CPC .. A61B 2017/00353; A61B 2018/1455; A61B 2018/1457; A61B 2018/00428; A61B 17/3209; A61B 2018/00404; A61B 2018/00601; A61B 2218/002; A61B 2218/001
See application file for complete search history.

(56) References Cited

U.S. PATENT DOCUMENTS

| D249,549 S | 9/1978 | Pike |
| D263,020 S | 2/1982 | Rau, III |

(Continued)

FOREIGN PATENT DOCUMENTS

| CN | 201299462 Y | 9/2009 |
| DE | 2415263 A1 | 10/1975 |

(Continued)

OTHER PUBLICATIONS

Michael Choti, "Abdominoperineal Resection with the LigaSure Vessel Sealing System and LigaSure Atlas 20 cm Open Instrument"; Innovations That Work, Jun. 2003.
(Continued)

*Primary Examiner* — Majid Jamialahmadi
(74) *Attorney, Agent, or Firm* — Carter, DeLuca & Farrell LLP

(57) ABSTRACT

A forceps includes a handle, a shaft having a proximal end coupled to the handle, and an end effector assembly coupled to a distal end of the shaft. The forceps includes a first jaw member and a second jaw member for grasping tissue therebetween. One or both of the first and second jaw members may include one or more needles extending therefrom. The one or more needles are in fluid communication with a fluid conduit extending along one or both of the first and second jaw members. The fluid conduit couples to a source of contrast agent to enable selective delivery of the contrast agent through the one or more needles.

16 Claims, 6 Drawing Sheets

Related U.S. Application Data

(60) Provisional application No. 62/131,956, filed on Mar. 12, 2015.

(51) Int. Cl.
*A61B 90/00* (2016.01)
*A61B 18/00* (2006.01)
*A61B 17/3209* (2006.01)
*A61B 18/12* (2006.01)
*A61B 34/35* (2016.01)

(52) U.S. Cl.
CPC ..... *A61B 34/35* (2016.02); *A61B 2017/00353* (2013.01); *A61B 2018/00404* (2013.01); *A61B 2018/00601* (2013.01); *A61B 2018/1226* (2013.01); *A61B 2018/1452* (2013.01); *A61B 2090/3925* (2016.02); *A61B 2090/3937* (2016.02); *A61B 2090/3954* (2016.02); *A61B 2218/002* (2013.01)

(56) References Cited

U.S. PATENT DOCUMENTS

| | | |
|---|---|---|
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| D384,413 S | 9/1997 | Zlock et al. |
| 5,704,925 A | 1/1998 | Otten |
| H1745 H | 8/1998 | Paraschac |
| 5,827,281 A | 10/1998 | Levin |
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| 6,408,203 B2 | 6/2002 | Mackin |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinge |
| D541,938 S | 5/2007 | Kerr et al. |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| 7,963,431 B2 | 6/2011 | Scirica |
| D649,249 S | 11/2011 | Guerra |
| D649,643 S | 11/2011 | Allen, IV et al. |
| D661,394 S | 6/2012 | Romero et al. |
| D670,808 S | 11/2012 | Moua et al. |
| D680,220 S | 4/2013 | Rachlin |
| 8,444,664 B2 | 5/2013 | Balanev et al. |
| 8,738,344 B2 | 5/2014 | Pichon et al. |
| 9,053,551 B2 | 6/2015 | Beymer et al. |
| 2003/0216733 A1* | 11/2003 | McClurken ............ A61B 18/14 606/51 |
| 2005/0159648 A1 | 7/2005 | Freed |
| 2008/0114381 A1* | 5/2008 | Voegele ................ A61B 17/10 606/151 |
| 2008/0125640 A1 | 5/2008 | Pichon et al. |
| 2011/0059023 A1 | 3/2011 | Tunnell |
| 2011/0112569 A1 | 5/2011 | Friedman et al. |
| 2011/0245844 A1* | 10/2011 | Jinno .................... A61B 34/30 606/130 |
| 2011/0251608 A1 | 10/2011 | Timm et al. |
| 2013/0035688 A1 | 2/2013 | Kerr et al. |
| 2013/0255063 A1 | 10/2013 | Hart et al. |
| 2013/0267947 A1 | 10/2013 | Orszulak |
| 2014/0114309 A1 | 4/2014 | Payne et al. |
| 2015/0272606 A1 | 10/2015 | Nobis |

FOREIGN PATENT DOCUMENTS

| | | |
|---|---|---|
| DE | 32514501 A1 | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 0712328 U1 | 3/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102006002179 B4 | 1/2009 |
| DE | 102008018406 B3 | 7/2009 |
| EP | 1281878 A1 | 2/2003 |
| EP | 1159926 A2 | 3/2003 |
| JP | 61501068 | 9/1984 |
| JP | 1024051 A | 1/1989 |
| JP | 1147150 A | 6/1989 |
| JP | 6502328 | 3/1992 |
| JP | 55106 | 1/1993 |
| JP | 0540112 | 2/1993 |
| JP | H0540112 A | 2/1993 |
| JP | 0006030945 | 2/1994 |
| JP | 6121797 A | 5/1994 |
| JP | 6285078 A | 10/1994 |
| JP | 06343644 | 12/1994 |
| JP | 6511401 | 12/1994 |
| JP | H06343644 A | 12/1994 |
| JP | 07265328 | 10/1995 |
| JP | H07265328 A | 10/1995 |
| JP | 08056955 | 3/1996 |

(56) References Cited

FOREIGN PATENT DOCUMENTS

| | | |
|---|---|---|
| JP | 856955 | 5/1996 |
| JP | 08252263 A | 10/1996 |
| JP | 8289895 A | 11/1996 |
| JP | 8317934 A | 12/1996 |
| JP | 8317936 A | 12/1996 |
| JP | 910223 A | 1/1997 |
| JP | 09000538 A | 1/1997 |
| JP | H0910223 A | 1/1997 |
| JP | 9122138 A | 5/1997 |
| JP | 0010000195 A | 1/1998 |
| JP | 10155798 A | 6/1998 |
| JP | 1147149 | 2/1999 |
| JP | 11070124 A | 3/1999 |
| JP | 11169381 A | 6/1999 |
| JP | 11192238 A | 7/1999 |
| JP | 11244298 | 9/1999 |
| JP | H11244298 A | 9/1999 |
| JP | 2000102545 A | 4/2000 |
| JP | 2000135222 A | 5/2000 |
| JP | 2000342599 A | 12/2000 |
| JP | 2000350732 A | 12/2000 |
| JP | 2001008944 | 1/2001 |
| JP | 2001029355 | 2/2001 |
| JP | 2001029356 | 2/2001 |
| JP | 2001003400 | 4/2001 |
| JP | 2001128990 A | 5/2001 |
| JP | 2001190564 A | 7/2001 |
| JP | 2002136525 A | 5/2002 |
| JP | 2002528166 A | 9/2002 |
| JP | 2003116871 A | 4/2003 |
| JP | 2003175052 A | 6/2003 |
| JP | 2003245285 A | 9/2003 |
| JP | 2004517668 A | 6/2004 |
| JP | 2004528869 A | 9/2004 |
| JP | 2005152663 A | 6/2005 |
| JP | 2005253789 A | 9/2005 |
| JP | 2005312807 A | 11/2005 |
| JP | 2006015078 A | 1/2006 |
| JP | 2006501939 A | 1/2006 |
| JP | 2006095316 A | 4/2006 |
| JP | 2008054926 A | 3/2008 |
| JP | 2011125195 A | 6/2011 |
| JP | H0630945 B2 | 11/2016 |
| SU | 401367 A1 | 11/1974 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 0245589 | 6/2002 |
| WO | 2006021269 A1 | 3/2006 |
| WO | 2005110264 A2 | 4/2006 |
| WO | 2008040483 A1 | 4/2008 |
| WO | 2011018154 A1 | 2/2011 |

OTHER PUBLICATIONS

Chung et al., "Clinical Experience of Sutureless Closed Hemorrhoidectomy with LigaSure" Diseases of the Colon & Rectum vol. 46, No. Jan. 1, 2003.

Tinkcler L.F., "Combined Diathermy and Suction Forceps", Feb. 6, 1967 (Feb. 6, 1967), British Medical Journal Feb. 6, 1976, vol. 1, nr. 5431 p. 361, ISSN: 0007-1447.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center,Charlotte,NC; Date: Aug. 2003.

Peterson et al. "Comparison of Healing Process Following Ligation with Sutures and Bipolar Vessel Sealing" Surgical Technology International (2001).

"Electrosurgery: A Historical Overview" Innovations in Electrosurgery; Sales/Product Literature; Dec. 31, 2000. (6 pages).

Johnson et al. "Evaluation of a Bipolar Electrothermal Vessel Sealing Device in Hemorrhoidectomy" Sales/Product Literature; Jan. 2004 (1 page).

E. David Crawford "Evaluation of a New Vessel Sealing Device in Urologic Cancer Surgery" Sales/Product Literature 2000.

Johnson et al. "Evaluation of the LigaSure Vessel Sealing System in Hemorrhoidectormy" American College of Surgeons (ACS) Clinicla Congress Poster (2000).

Muller et al., "Extended Left Hemicolectomy Using the LigaSure Vessel Sealing System" Innovations That Work, Sep. 1999.

Kennedy et al. "High-burst-strength, feedback-controlled bipolar vessel sealing" Surgical Endoscopy (1998) 12: 876-878.

Burdette et al. "In Vivo Probe Measurement Technique For Determining Dielectric Properties at VHF Through Microwave Frequencies", IEEE Transactions on Microwave Theory and Techniques, vol. MTT-28, No. 4, Apr. 1980 pp. 414-427.

Carus et al., "Initial Experience With the LigaSure Vessel Sealing System in Abdominal Surgery" Innovations That Work, Jun. 2002.

Heniford et al. "Initial Results with an Electrothermal Bipolar Vessel Sealer" Surgical Endoscopy (2000) 15:799-801. (4 pages).

Herman et al., "Laparoscopic Intestinal Resection With the LigaSure Vessel Sealing System: A Case Report" Innovations That Work, Feb. 2002.

Koyle et al., "Laparoscopic Palomo Varicocele Ligation in Children and Adolescents" Pediatric Endosurgery & Innovative Techniques, vol. 6, No. 1, 2002.

W. Scott Helton, "LigaSure Vessel Sealing System: Revolutionary Hemostasis Product for General Surgery"; Sales/Product Literature 1999.

LigaSure Vessel Sealing System, the Seal of Confidence in General, Gynecologic, Urologic, and Laparaoscopic Surgery; Sales/Product Literature; Apr. 2002.

Joseph Ortenberg "LigaSure System Used in Laparoscopic 1st and 2nd Stage Orchiopexy" Innovations That Work, Nov. 2002.

Sigel et al. "The Mechanism of Blood Vessel Closure by High Frequency Electrocoagulation" Surgery Gynecology & Obstetrics, Oct. 1965 pp. 823-831.

Sampayan et al., "Multilayer Ultra-High Gradient Insulator Technology" Discharges and Electrical Insulation in Vacuum, 1998. Netherlands Aug. 17-21, 1998; vol. 2, pp. 740-743.

Paul G. Horgan, "A Novel Technique for Parenchymal Division During Hepatectomy" The American Journal of Surgery, vol. 181, No. 3, Apr. 2001 pp. 236-237.

Benaron et al., "Optical Time-Of-Flight and Absorbance Imaging of Biologic Media", Science, American Association for the Advancement of Science, Washington, DC, vol. 259, Mar. 5, 1993, pp. 1463-1466.

Olsson et al. "Radical Cystectomy in Females" Current Surgical Techniques in Urology, vol. 14, Issue 3, 2001.

Palazzo et al. "Randomized clinical trial of Ligasure versus open haemorrhoidectomy" British Journal of Surgery 2002, 89, 154-157.

Levy et al. "Randomized Trial of Suture Versus Electrosurgical Bipolar Vessel Sealing in Vaginal Hysterectomy" Obstetrics & Gynecology, vol. 102, No. 1, Jul. 2003.

"Reducing Needlestick Injuries in the Operating Room" Sales/Product Literature 2001. (1 page).

Bergdahl et al. "Studies on Coagulation and the Development of an Automatic Computerized Bipolar Coagulator" J. Neurosurg, vol. 75, Jul. 1991, pp. 148-151.

Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.

Sayfan et al. "Sutureless Closed Hemorrhoidectomy: A New Technique" Annals of Surgery vol. 234 No. Jul. 1, 2001; pp. 21-24.

Levy et al., "Update on Hysterectomy—New Technologies and Techniques" OBG Management, Feb. 2003. (15 pages).

Dulemba et al. "Use of a Bipolar Electrothermal Vessel Sealer in Laparoscopically Assisted Vaginal Hysterectomy" Sales/Product Literature; Jan. 2004.

Strasberg et al., "Use of a Bipolar Vessel-Sealing Device for Parenchymal Transection During Liver Surgery" Journal of Gastrointestinal Surgery, vol. 6, No. 4, Jul /Aug. 2002 pp. 569-574.

(56) References Cited

OTHER PUBLICATIONS

Sengupta et al., "Use of a Computer-Controlled Bipolar Diathermy System in Radical Prostatectomies and Other Open Jrological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surger" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.. (1 page).
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
U.S. Appl. No. 08/926,869; filed Sep. 10, 1997; inventor: James G. Chandler.
U.S. Appl. No. 09/177,950; filed Oct. 23, 1998; inventor: Randel A. Frazier.
U.S. Appl. No. 09/387,883; filed Sep. 1, 1999; inventor: Dale F. Schmaltz.
U.S. Appl. No. 09/591,328; filed Jun. 9, 2000; inventor: Thomas P. Ryan.
U.S. Appl. No. 12/336,970; filed Dec. 17, 2008; inventor: Paul R. Sremeich.
U.S. Appl. No. 14/065,644; filed Oct. 29, 2013; inventor: Reschke.
Heniford et al. "Initial Research and Clinical Results with an Electrothermal Bipolar Vessel Sealer" Oct. 1999.
Search Report issued in corresponding International PCT Application No. PCT/US2015/057776 dated Jan. 21, 2016.
Michael Choti, "Abdominoperineal Resection with the LigaSure Vessel Sealing System and LigaSure Atlas 20 cm Open Instrument"; Innovations That Work, Jun. 2003, 4 pages.
Chung et al., "Clinical Experience of Sutureless Closed Hemorrhoidectomy with LigaSure" Diseases of the Colon & Rectum vol. 46, No. Jan. 1, 2003, pp. 87-92.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte,NC; Date: Aug. 2003, 1 page.
Peterson et al. "Comparison of Healing Process Following Ligation with Sutures and Bipolar Vessel Sealing" Surgical Technology International (2001). (8 pages).

E. David Crawford "Evaluation of a New Vessel Sealing Device in Urologic Cancer Surgery" Sales/Product Literature 2000, 1 page.
Johnson et al. "Evaluation of the LigaSure Vessel Sealing System in Hemorrhoidectormy" American College of Surgeons (ACS) Clinicla Congress Poster (2000), 1 page.
Muller et al., "Extended Left Hemicolectomy Using the LigaSure Vessel Sealing System" Innovations That Work, Sep. 1999. (4 pages).
Carus et al., "Initial Experience With the LigaSure Vessel Sealing System in Abdominal Surgery" Innovations That Work, Jun. 2002, 4 pages.
Herman et al., "Laparoscopic Intestinal Resection With the LigaSure Vessel Sealing System: A Case Report"; Innovations That Work, Feb. 2002, 4 pages.
Koyle et al., "Laparoscopic Palomo Varicocele Ligation in Children and Adolescents" Pediatric Endosurgery & Innovative Techniques, vol. 6, No. 1, 2002, pp. 15-19.
W. Scott Helton, "LigaSure Vessel Sealing System: Revolutionary Hemostasis Product for General Surgery"; Sales/Product Literature 1999, 1 page.
LigaSure Vessel Sealing System, the Seal of Confidence in General, Gynecologic, Urologic, and Laparaoscopic Surgery; Sales/Product Literature; Apr. 2002, 8 pages.
Joseph Ortenberg "LigaSure System Used in Laparoscopic 1st and 2nd Stage Orchiopexy" Innovations That Work, Nov. 2002, 4 pages.
Olsson et al. "Radical Cystectomy in Females" Current Surgical Techniques in Urology, vol. 14, Issue 3, 2001, 8 pages.
Levy et al. "Randomized Trial of Suture Versus Electrosurgical Bipolar Vessel Sealing in Vaginal Hysterectomy" Obstetrics & Gynecology, vol. 102, No. 1, Jul. 2003, pp. 147-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001, 1 page.
Dulemba et al. "Use of a Bipolar Electrothermal Vessel Sealer in Laparoscopically Assisted Vaginal Hysterectomy" Sales/Product Literature; Jan. 2004, 1 page.
Rothenberg et al. "Use of the LigaSure Vessel Sealing System in Minimally Invasive Surgery in Children" Int'l Pediatric Endosurgery Group (IPEG) 2000, 1 page.
Crawford et al. "Use of the LigaSure Vessel Sealing System in Urologic Cancer Surgery"; Grand Rounds in Urology 1999 Vol 1 Issue 4 pp. 10-17.
Craig Johnson, "Use of the LigaSure Vessel Sealing System in Bloodless Hemorrhoidectomy" Innovations That Work, Mar. 2000, 4 pages.
Levy et al. "Use of a New Energy-based Vessel Ligation Device During Vaginal Hysterectomy" Int'l Federation of Gynecology and Obstetrics (FIGO) World Congress 1999, 1 page.
E. David Crawford "Use of a Novel Vessel Sealing Technology in Management of the Dorsal Veinous Complex" Sales/Product Literature 2000, 1 page.
Jarrett et al., "Use of the LigaSure Vessel Sealing System for Peri-Hilar Vessels in Laparoscopic Nephrectomy" Sales/Product Literature 2000, 1 page.
McLellan et al. "Vessel Sealing for Hemostasis During Pelvic Surgery" Int'l Federation of Gynecology and Obstetrics FIGO World Congress 2000, Washington, D.C., 1 page.
McLellan et al. "Vessel Sealing for Hemostasis During Gynecologic Surgery" Sales/Product Literature 1999, 1 page.
Heniford et al. "Initial Research and Clinical Results with an Electrothermal Bipolar Vessel Sealer" Oct. 1999. (1 page).

* cited by examiner

MAPPING VESSELS FOR RESECTING BODY TISSUE

CROSS REFERENCE TO RELATED APPLICATIONS

The present application is a division of U.S. patent application Ser. No. 14/923,629, filed Oct. 27, 2015, which claims the benefit U.S. Provisional Application Ser. No. 62/131,956, filed on Mar. 12, 2015, the entire contents of each of which are incorporated herein by reference.

TECHNICAL FIELD

The present disclosure relates to surgical devices, systems, and methods for performing surgical resection procedures, and, more particularly, to surgical devices, systems, and methods for mapping vessels during segmental resection procedures.

BACKGROUND

In general, resection is a surgical procedure that involves removing body tissue to combat certain unhealthy body conditions such as suppurative lesions and nonmalignant masses. Some experts also recommend it for removal of cancerous tissue. Segmental resection or segmentectomy is a surgical procedure to remove a portion of body tissue such as an organ or gland. For example, lung segmentectomy is a procedure that involves removing lung disease, fungal infections, and/or congenital lung malformations without removing excess normal lung. Although extensive lung resections such as lobectomy and pneumonectomy may provide optimal results, many thoracic patients have chronic obstructive pulmonary disease (COPD) or emphysema and cannot tolerate such extensive lung resections due to their minimal lung reserve. During lung resection procedures, clinicians are faced with the challenge of identifying an appropriate line segment for cutting to establish the most suitable resection margin and are often required to speculate as to the location of the most effective cutting line segment. In this regard, the clinician's conjecture undesirably risks removal of excess normal tissue.

SUMMARY

Accordingly, new devices, systems, and methods for more effectively resecting tissue would be useful. In particular, devices, systems, and methods that enable a clinician to identify precise cut lines through vessel mapping would facilitate quick and accurate transections, thereby maximizing lung reserve while effectively removing unhealthy tissue.

In one aspect, the present disclosure relates to a forceps including a handle, a shaft having proximal and distal ends, and an end effector assembly including a first jaw member and a second jaw member. The proximal end of the shaft is coupled to the handle and the distal end of the shaft is coupled to the end effector assembly.

One or both of the first and second jaw members is movable relative to the other jaw member between a spaced-apart position and an approximated position for grasping tissue therebetween. In embodiments, the first and second jaw members each include an electrically-conductive tissue-contacting surface configured to connect to a source of energy to treat tissue grasped between the first and second jaw members.

One or both of the first and second jaw members may include one or more needles extending therefrom. The one or more needles are in fluid communication with a fluid conduit extending along one or both of the first and second jaw members. The fluid conduit may be defined within one or both of the first and second jaw members. In some embodiments, the fluid conduit extends along an outer surface of one or both of the first and second jaw members. The fluid conduit is configured to couple to a source of contrast agent to enable selective delivery of the contrast agent through the one or more needles. The one or more needles may include a microneedle. In some embodiments, the contrast agent is stored within the handle. The contrast agent may include ultrasound markers, computed tomography markers, magnetic resonance imaging makers, fluorescent markers, or combinations thereof.

According to yet another aspect, the present disclosure is directed to a method of resecting tissue. The method involves locating a vessel, clamping the vessel to create a boundary for the delivery of a contrast agent to predetermined portions of tissue, injecting the contrast agent into the vessel, creating images of the tissue based upon the location of the contrast agent within the tissue, identifying a cut line based on the images created with the contrast agent, and cutting the tissue along the cut line to resect predetermined portions of the tissue.

Injecting the contrast agent into the vessel may include delivering the contrast agent through one or more needles of an end effector assembly used to clamp the vessel.

The vessel may be in fluid communication with an organ, a gland, or combinations thereof. For example, the vessel may be in fluid communication with lung tissue and/or with liver tissue. The vessel may include a bile duct.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Figure 1:
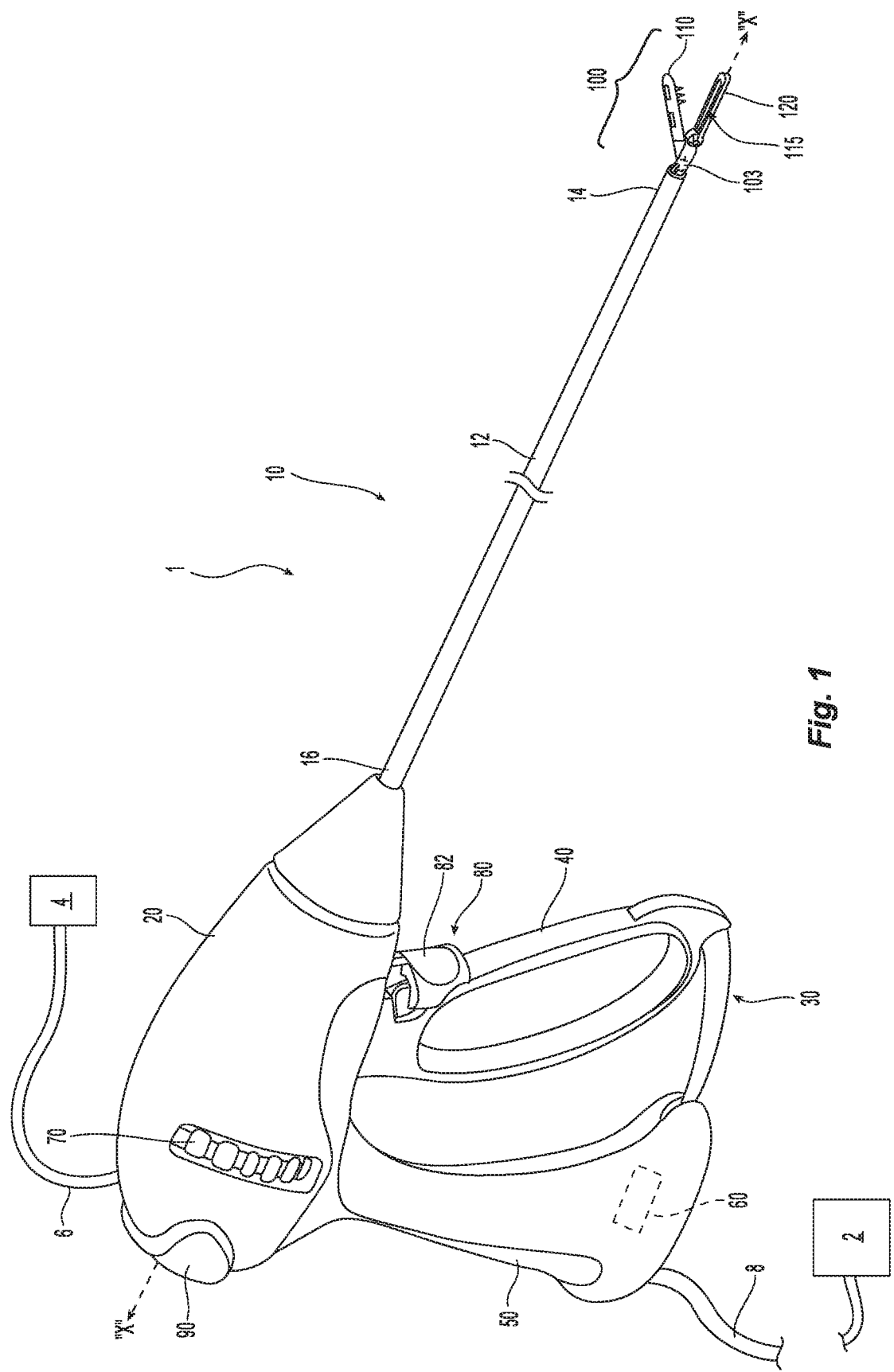
FIG. 1 is a perspective view of a surgical system according to the principles of the present disclosure with an end effector assembly of a forceps thereof shown in a spaced-apart position.

Particular embodiments of the present disclosure are described hereinbelow with reference to the accompanying drawings in which like reference numerals designate identical or corresponding elements in each of the several views. As used herein the term "distal" refers to that portion of the system, device and/or component(s) thereof, that are farther from the user, while the term "proximal" refers to that portion of the system, device and/or component(s) thereof, that are closer to the user. In the following description, well-known functions or constructions are not described in detail to avoid obscuring the present disclosure in unnecessary detail.

Surgical systems in accordance with the present disclosure can include endoscopic and/or open surgical instruments such as forceps devices, stapling devices, ultrasonic dissection devices, and/or any other suitable surgical devices. Obviously, different electrical and mechanical connections and considerations apply to each particular type of device; however, the aspects and features of the present disclosure remain generally consistent regardless of the particular device used. For a detailed discussion of the construction and operation of example surgical devices, reference may be made to U.S. Patent Application Publication No. 2013/0267947, U.S. Patent Application Publication No. 2013/0255063, U.S. Pat. No. 7,963,431, and/or U.S. Pat. No. 8,444,664, the entirety of each of which is incorporated herein by reference.

In the interest of brevity, surgical systems of the present disclosure will only be described herein in connection with an endoscopic forceps.

Turning now to FIG. 1, one embodiment of a surgical system 1 includes an electrosurgical energy source 2 (e.g., a generator or other suitable power source), a contrast agent source 4 configured to dispense contrast agent (e.g., ultrasound markers, computed tomography markers, magnetic resonance imaging makers, fluorescent markers, or combinations thereof), and an endoscopic forceps 10 in communication with the energy source 2 and contrast agent source 4. Forceps 10 defines a longitudinal axis "X-X" and includes a housing 20, a handle assembly 30, a rotating assembly 70, a trigger assembly 80 and an end effector assembly 100. In some embodiments, contrast agent source 4 can be supported within forceps 10 (e.g., within housing 20 and/or handle assembly 30). Forceps 10 further includes a shaft 12 having a distal end 14 configured to mechanically engage end effector assembly 100 and a proximal end 16 that mechanically engages housing 20. End effector assembly 100 includes first and second jaw members 110, 120. Forceps 10 also includes cable 8 that connects forceps 10 to energy source 2; although forceps 10 may alternatively be configured as a battery-powered device. Cable 8 includes a wire (or wires) (not shown) extending therethrough that has sufficient length to extend through shaft 12 in order to provide energy to tissue-contacting surfaces of one or both jaw members 110, 120, respectively. An activation switch 90 is provided on housing 20 for enabling application of selective energy to jaw members 110, 120.

With continued reference to FIG. 1, handle assembly 30 includes a fixed handle 50 and a moveable handle 40. Fixed handle 50 is integrally associated with housing 20 and movable handle 40 is moveable relative to fixed handle 50. In some embodiments, movable handle 40, fixed handle 50, and/or housing 20 support a ratcheting assembly 60 that enables movable handle 40 to be positioned in a plurality of separate and discrete positions relative to fixed handle 50. Rotating assembly 70 is rotatable in either direction about longitudinal axis "X-X" to rotate end effector 100 about longitudinal axis "X-X." Housing 20 supports internal working components (not shown) of forceps 10.

Continuing with reference to FIG. 1, moveable handle 40 of handle assembly 30 is ultimately connected to a drive assembly (not shown) that, together, mechanically cooperate to impart movement of jaw members 110 and 120 between a spaced-apart position and one or more approximated positions to grasp tissue disposed between jaw members 110, 120. As shown in FIG. 1, moveable handle 40 is initially spaced-apart from fixed handle 50 and, correspondingly, jaw members 110, 120 are in the spaced-apart position. Moveable handle 40 is depressible from this initial position to one or more depressed positions corresponding to one or more approximated positions of jaw members 110, 120. For example, in some embodiments, one approximated position can be a clamping position defining a first height "H1" between jaw members 110, 210 (see FIG. 2A) and another approximated position can be a sealing position defining a second height "H2" between jaw members 110, 210 (see FIG. 2B) that is different from first height "H1." For example, first height "H1" can be larger than second height "H2." One or more of the approximated positions can correspond to one or more of the plurality of separate and discrete positions of movable handle 40 relative to fixed handle 50.

In some embodiments, a knife assembly (not shown) is provided. Trigger 82 of trigger assembly 80 is operably coupled to the knife assembly (not shown) for selectively translating a knife blade (not shown) through a knife channel 115 defined within one or both of jaw members 110, 120 to cut tissue disposed between jaw members 110, 120.

Figure 2A:
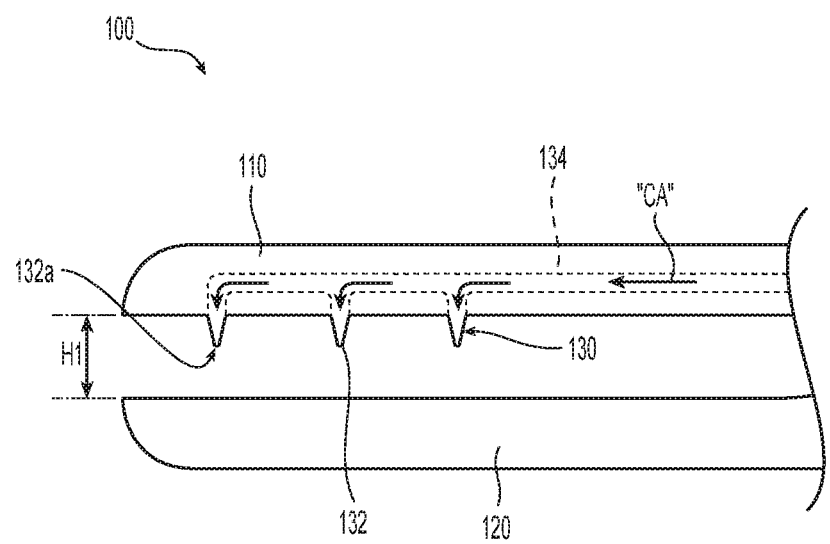
FIGS. 2A and 2B are enlarged, partial side views of the end effector assembly of the surgical system of FIG. 1 in various approximated positions.
Figure 2B:
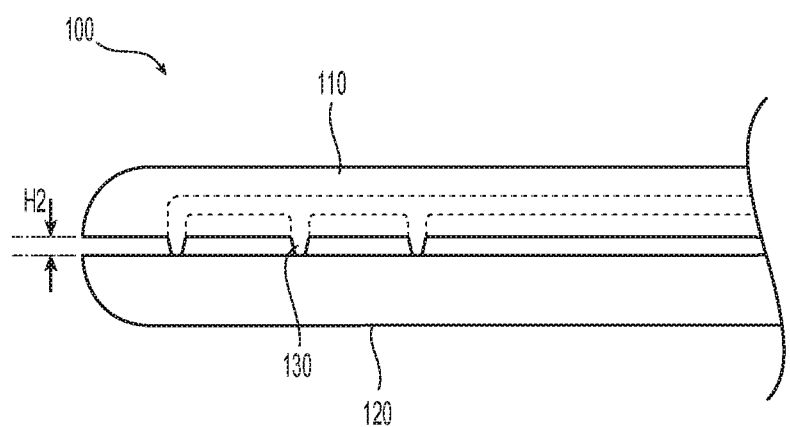

Referring to FIGS. 2A and 2B, end effector assembly 100 includes a needle assembly 130 having one or more needles 132 that define distal openings 132a. The one or more needles 132 may be sharpened. Needles 132 may be microneedles or needles of micro convention size. The needles 132 can extend from one or both of first and second jaw members 110, 120. Each needle 132 is in fluid communication with a fluid conduit 134 that may be defined within one or both of first and second jaw members 110, 120. In some embodiments, fluid conduit 134 extends alongside an outer surface of one or both of first and second jaw members 110, 120. Fluid conduit 134 couples to contrast agent source 4 via a contrast agent conduit 6 (see FIG. 1). Fluid conduit 134 and contrast agent conduit 6 may be integrally formed.

Figure 3:
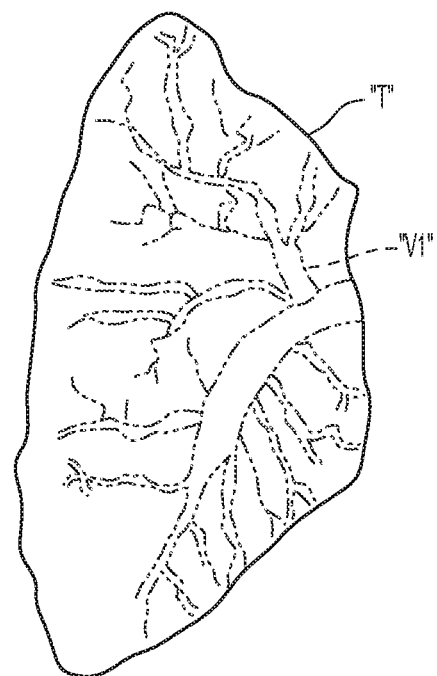
FIG. 3 is a front, elevational view of lung tissue.
Figure 4:
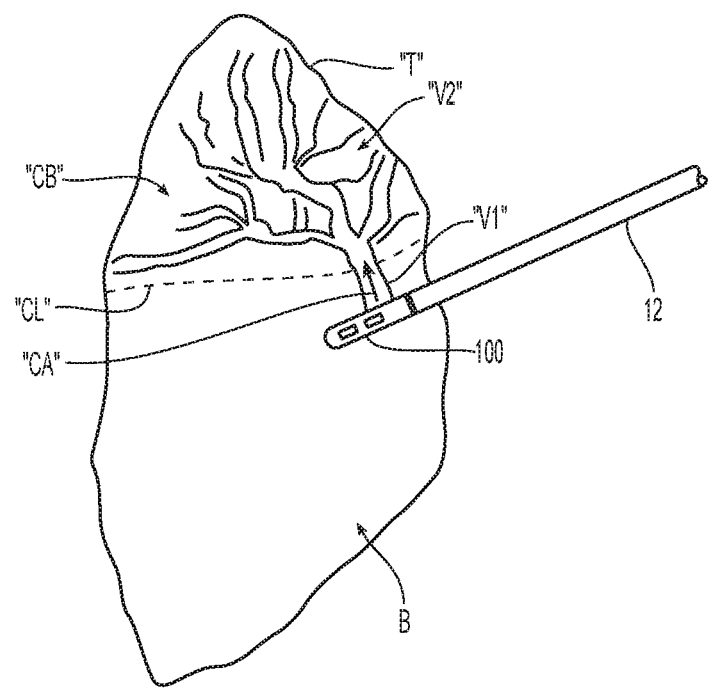
FIG. 4 is a front, elevational view illustrating the end effector assembly of FIG. 2 being used to identify a cut line for resecting the lung tissue.

In operation as seen in FIGS. 3 and 4, a clinician locates a vessel, which may be a first vessel "V1," of an organ, gland, or other suitable tissue to clamp with forceps 10 for effectuating a resection procedure and/or for identifying/mapping vessels and/or tissue that the located vessel feeds to ensure proper/desired dissection. While forceps 10 is clamped on the located vessel, for example, with needles 132 thereof deployed and/or retracted, and/or with a separate needless forceps (not shown), a clinician can advantageously determine (e.g., via MRI, CT, etc.) which structures/tissue that would be deprived of blood before any cutting is effectuated. In the illustrated embodiment, tissue "T" is lung tissue; however, the presently described devices, systems, and methods can be applied to any suitable tissue. For example, the first vessel "V1" may be in fluid communication with liver tissue where the first vessel "V1" vessel may include a bile duct.

After locating the first vessel "V1," the clinician approximates first and second jaw members 110, 120 to the clamping position (FIG. 2A) to clamp the first vessel "V1"

between tissue-contacting surfaces of first and second jaw members 110, 120. In the clamping position, needles 132 puncture the first vessel "V1" so that needles 132 are in fluid communication with first vessel "V1." The clamping of first and second jaw members 110, 120 to the first vessel "V1" creates a boundary for the delivery of contrast agent to predetermined portions of the tissue "T." Contrast agent "CA" is then advanced through fluid conduit 134 and out of needles 132 for delivery into the first vessel "V1." In this regard, the contrast agent "CA" is fed into one or more secondary vessels "V2" in fluid communication with the first vessel "V1." The created boundary prevents the contrast agent "CA" from feeding into one or more vessels of a blocked area "B." Images of the tissue "T" can then be created (e.g., CT, MIll, etc.) based upon a location of the contrast agent "CA" within the tissue "T." In this regard, only the one or more secondary vessels "V2" in an unblocked area "UB" of the tissue "T" will "light up" on the created image as seen in FIG. 4, effectively mapping the blocked and unblocked areas "B," "UB" on the created image. If the first vessel "V1" does not provide the desired mapping, the process can be repeated on other vessels as desired.

With the distinct separation between the blocked and unblocked areas "B," "UB," the clinician can identify a cut line "CL" based on the images created with the contrast agent "CA." In this regard, the tissue "T" can be quickly and accurately cut (e.g., with a scalpel or other suitable cutting device) along the cut line "CL" to resect the tissue "T" and efficiently remove any unhealthy tissue while maximizing lung reserve of healthy tissue. After establishing the cut line "CL," the clinician can further approximate first and second jaw members 110, 120 into the sealing position (FIG. 2B) and activate electrosurgical energy from the electrosurgical energy source 2 to seal the first vessel "V1" as desired. The forceps 10 can then be removed.

Figure 5:
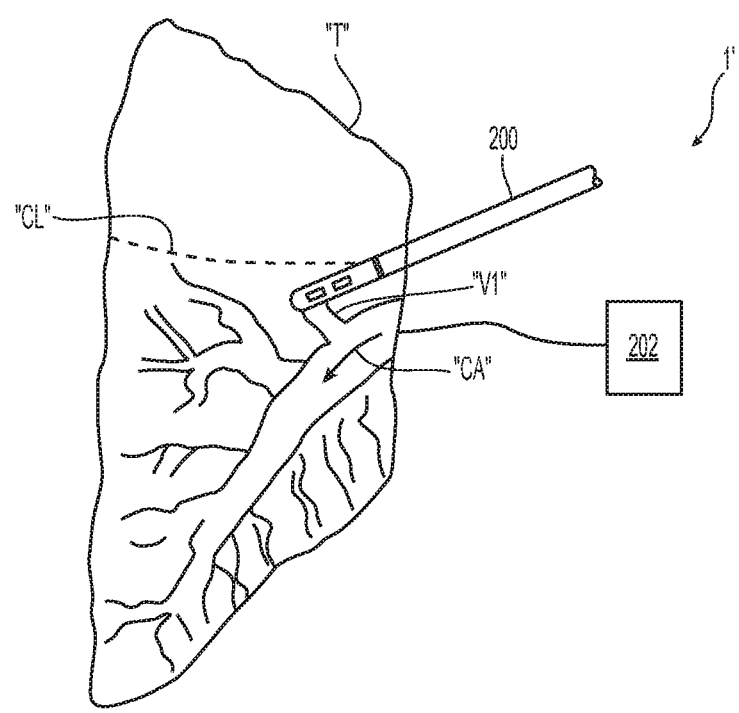
FIG. 5 is a front, elevational view of another embodiment of a surgical system according to the principles of the present disclosure, the surgical system being used identify a cut line for resecting the lung tissue.

As seen in FIG. 5, another embodiment of a surgical system 1' includes a forceps 200 and a contrast agent source 202 that is separate and distinct from forceps 200. In some embodiments, contrast agent source 202 can be a syringe filled with any of the presently described contrast agents.

In operation, forceps 200 clamps to the first vessel "V1" and contrast agent "CA" can be delivered to the first vessel "V1" separate from forceps 200 (e.g., intravenously) without having to pass through forceps 200. The contrast agent "CA" can be delivered to the first vessel "V1" before, during, and/or after forceps 200 is clamped to the first vessel "V1." The cut line "CL" can then be identified and the tissue "T" resected as described above with respect to surgical system 1.

Figure 6:
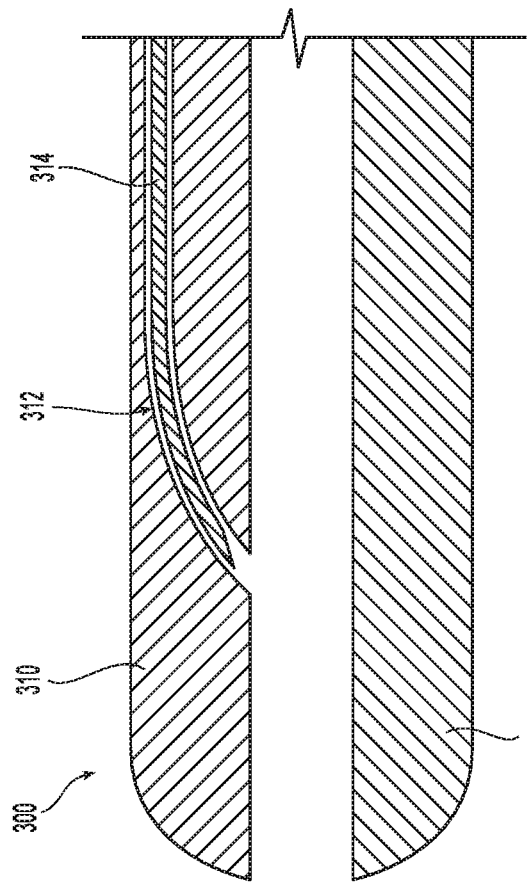
FIGS. 6 and 7 are progressive views of another embodiment of an end effector assembly in accordance with the present disclosure.
Figure 7:
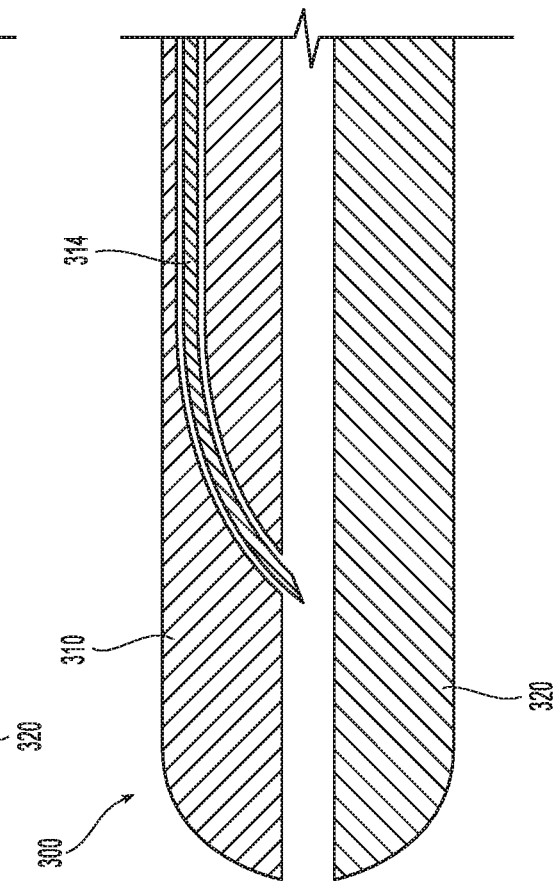

With reference to FIGS. 6 and 7, one embodiment of an end effector assembly 300 includes a pair of jaw members 310, 320 and one or more needles 314 that can be deployed or retracted through one or more channels 312 defined through jaw member 310 (and/or jaw member 320). Needle 314 may be selectively deployed or retracted relative to jaw member 310 via any suitable drive assembly (not shown). For example, as seen in FIG. 6, needle 314 may be retracted or retained within channel 312 when jaw members 310, 320 are open or substantially open (FIG. 6) to protect vessels and/or tissue from being undesirably punctured, and when desired (e.g., when jaw members 310, 320 are closed or substantially closed as seen in FIG. 7), deployed as necessary to puncture tissue to enable delivery of a contrast agent or the like through channel 312 of jaw member 310 and/or through needle 314. In some embodiments, needle 314 defines a fluid conduit therethrough configured to receive and deliver the contrast agent therethrough.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Figure 8:
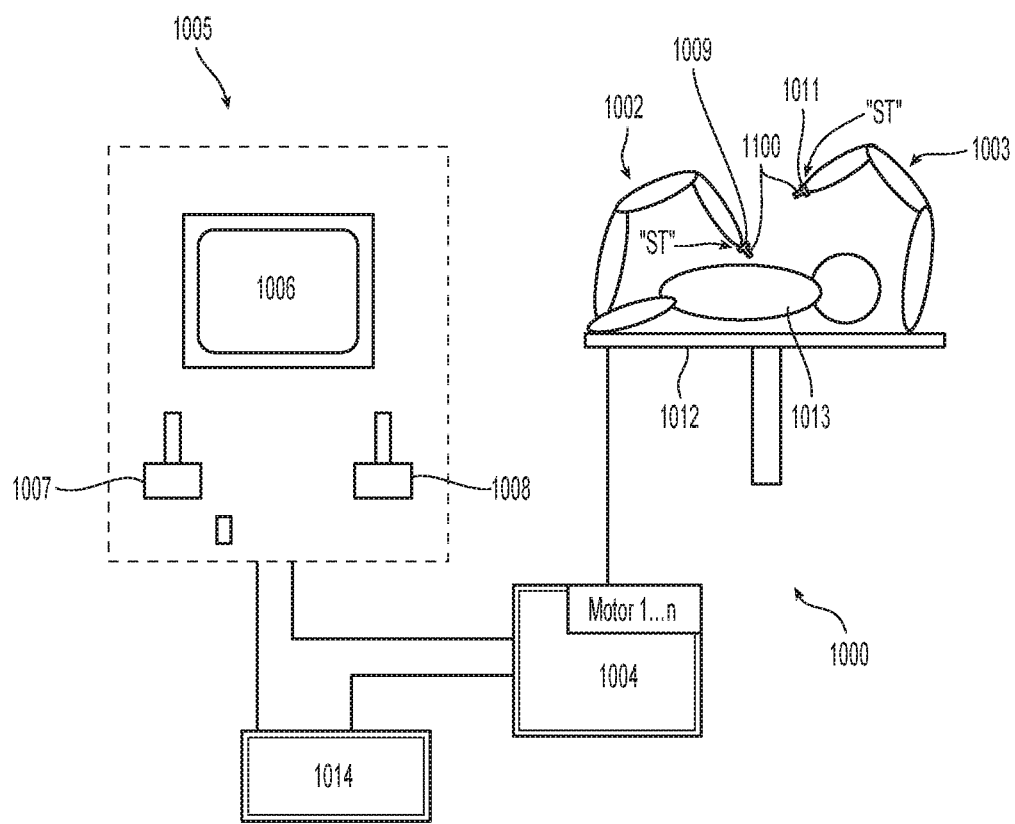
FIG. 8 is a schematic illustration of a medical work station and operating console in accordance with the present disclosure.

Referring also to FIG. 8, a medical work station is shown generally as work station 1000 and generally may include a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person (not shown), for example a surgeon, may be able to telemanipulate robot arms 1002, 1003 in a first operating mode.

Each of the robot arms 1002, 1003 may include a plurality of members, which are connected through joints, and an attaching device 1009, 1011, to which may be attached, for example, a surgical tool "ST" supporting an end effector 1100, in accordance with any one of several embodiments disclosed herein, as will be described in greater detail below.

Robot arms 1002, 1003 may be driven by electric drives (not shown) that are connected to control device 1004. Control device 1004 (e.g., a computer) may be set up to activate the drives, in particular by means of a computer program, in such a way that robot arms 1002, 1003, their attaching devices 1009, 1011 and thus the surgical tool (including end effector 1100) execute a desired movement according to a movement defined by means of manual input devices 1007, 1008. Control device 1004 may also be set up in such a way that it regulates the movement of robot arms 1002, 1003 and/or of the drives.

Medical work station 1000 may be configured for use on a patient 1013 lying on a patient table 1012 to be treated in a minimally invasive manner by means of end effector 1100. Medical work station 1000 may also include more than two robot arms 1002, 1003, the additional robot arms likewise being connected to control device 1004 and being telemanipulatable by means of operating console 1005. A medical instrument or surgical tool (including an end effector 1100) may also be attached to the additional robot arm. Medical work station 1000 may include a database 1014, in particular coupled to with control device 1004, in which are stored, for example, pre-operative data from patient/living being 1013 and/or anatomical atlases.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A forceps, comprising:
a handle;
a shaft having proximal and distal ends, the proximal end coupled to the handle;
an end effector assembly coupled to the distal end of the shaft and including a first jaw member and a second jaw member, at least one of the first or second jaw members movable relative to the other jaw member between a spaced-apart position and an approximated position for grasping tissue therebetween, one of the first or second jaw members including at least one needle extending therefrom and defining a channel therein that retains the at least one needle within the channel, the at least one needle and the channel are both in fluid communication with a source of contrast agent to enable selective delivery of the contrast agent through the at least one needle and through the channel around an outer surface of the at least one needle.

2. The forceps according to claim 1, wherein the at least one needle includes a plurality of needles.

3. The forceps according to claim 1, wherein the first and second jaw members each include an electrically-conductive tissue-contacting surface configured to connect to a source of energy to treat tissue grasped between the first and second jaw members.

4. The forceps according to claim 1, wherein the contrast agent is stored within the handle.

5. The forceps according to claim 4, wherein the contrast agent includes ultrasound markers, computed tomography markers, magnetic resonance imaging makers, fluorescent markers, or combinations thereof.

6. The forceps according to claim 1, wherein the at least one needle extends to a tip configured to deliver the contrast agent therethrough.

7. A forceps, comprising:
a handle;
a shaft having proximal and distal ends, the proximal end coupled to the handle;
an end effector assembly coupled to the distal end of the shaft and including a first jaw member and a second jaw member, at least one of the first or second jaw members movable relative to the other jaw member between a spaced-apart position and an approximated position for grasping tissue therebetween, one of the first or second jaw members including at least one needle movable relative to the first and second jaw members, the at least one needle in fluid communication with a source of contrast agent to enable selective delivery of the contrast agent through the at least one needle into predetermined portions of tissue bound by the first and second jaw members when the first and second jaw members are disposed in the approximated position, wherein the one of the first or second jaw members defines a channel therein that supports the at least one needle, the channel disposed in fluid communication with the contrast agent to enable selective advancement of the contrast agent through the at least one needle and through the channel around an outer surface of the at least one needle.

8. The forceps according to claim 7, wherein the channel retains the at least one needle in the channel.

9. The forceps according to claim 7, wherein the at least one needle is movable through the channel between a first position in which the at least one needle is retracted within the channel and a second position in which the at least one needle is deployed from the channel.

10. The forceps according to claim 7, wherein the channel is sufficiently large enough to enable the contrast agent to advance around the outer surface of the at least one needle.

11. The forceps according to claim 7, wherein the at least one needle extends to a tip configured to deliver the contrast agent therethrough.

12. A robotic surgical system, comprising:
a robotic arm;
a forceps coupled to the robotic arm, the forceps including:
a shaft having proximal and distal ends;
an end effector assembly coupled to the distal end of the shaft and including a first jaw member and a second jaw member, at least one of the first or second jaw members movable relative to the other jaw member between a spaced-apart position and an approximated position for grasping tissue therebetween, one of the first or second jaw members including at least one needle, the at least one needle in fluid communication with a source of contrast agent to enable selective delivery of the contrast agent through the at least one needle into predetermined portions of tissue bound by the first and second jaw members when the first and second jaw members are disposed in the approximated position, wherein the one of the first or second jaw members defines a channel therein that retains the at least one needle within the channel, wherein the channel is disposed in fluid communication with the contrast agent to enable selective advancement of the contrast agent through the at least one needle and through the channel around an outer surface of the at least one needle.

13. The robotic surgical system of claim 12, wherein the at least one needle is movable relative to the first and second jaw members.

14. The robotic surgical system of claim 12, wherein the at least one needle is movable through the channel between a first position in which the at least one needle is retracted within the channel and a second position in which the at least one needle is deployed from the channel.

15. The robotic surgical system according to claim 12, wherein the channel is large enough to enable the contrast agent to advance around the outer surface of the at least one needle.

16. The robotic surgical system according to claim 12, wherein the at least one needle extends to a tip configured to deliver the contrast agent therethrough.

\* \* \* \* \*